(12) United States Patent
Gerber (10) Patent No.: US 9,744,336 B2
(45) Date of Patent: Aug. 29, 2017

(54) DEVICE FOR GRAVITY-DRIVEN CONTROL OF THE FILLING PRESSURE OF A CATHETER BALLOON

(71) Applicant: University of Zurich, Zurich (CH)

(72) Inventor: Andreas Christian Gerber, Gockhausen (CH)

(73) Assignee: UNIVERSITY OF ZURICH, Zurich (CH)

( * ) Notice: Subject to any disclaimer, the term of this patent is extended or adjusted under 35 U.S.C. 154(b) by 458 days.

(21) Appl. No.: 14/386,739

(22) PCT Filed: Mar. 22, 2013

(86) PCT No.: PCT/EP2013/056169
§ 371 (c)(1),
(2) Date: Sep. 19, 2014

(87) PCT Pub. No.: WO2013/139986
PCT Pub. Date: Sep. 26, 2013

(65) Prior Publication Data
US 2015/0080793 A1    Mar. 19, 2015

(30) Foreign Application Priority Data
Mar. 22, 2012    (DE) ......................... 10 2012 005 643

(51) Int. Cl.
*A61M 29/00* (2006.01)
*A61M 25/10* (2013.01)
*A61M 16/04* (2006.01)

(52) U.S. Cl.
CPC .... *A61M 25/10185* (2013.11); *A61M 16/044* (2013.01); *A61M 25/1018* (2013.01); *A61M 25/10182* (2013.11); *A61M 25/10187* (2013.11)

(58) Field of Classification Search
CPC ........ A61M 25/1018; A61M 25/10187; A61M 25/10181; A61M 25/10182;
(Continued)

(56) References Cited

U.S. PATENT DOCUMENTS

| 3,654,802 A | 4/1972 | Falconer |
| 4,182,344 A | 1/1980 | Benson |

(Continued)

FOREIGN PATENT DOCUMENTS

| FR | 2 940 621 | 7/2010 |
| GB | 891026 | 3/1962 |

(Continued)

OTHER PUBLICATIONS

International Search Report dated Jun. 24, 2013 from PCT/EP2013/056169.

*Primary Examiner* — Kevin C Sirmons
*Assistant Examiner* — Leah Swanson
(74) *Attorney, Agent, or Firm* — Swanson & Bratschun, L.L.C.

(57) ABSTRACT

Device for gravity-driven, particularly continuous, control of the filling pressure in a balloon catheter (3), comprising: a balloon reservoir that is statically loaded with a vertically guided weight guide or stamp (9) that weighs vertically on the balloon reservoir, wherein said weight guide or stamp is designed to carry vertically arranged and therewith plumb-vertically acting weight elements (8), and wherein the balloon reservoir is guided in a cylindrical shell (6).

24 Claims, 7 Drawing Sheets (58) Field of Classification Search
CPC .... A61M 25/010184; A61M 25/10185; A61M 25/10186; A61M 25/10; A61M 16/04; A61M 16/044; A61M 16/0409; A61M 16/0434
USPC ..... 604/97.01–97.03, 100.01, 100.02, 96.01; 128/207.14, 207.15, 205.23
See application file for complete search history.

(56) References Cited

U.S. PATENT DOCUMENTS

| | | | |
|---|---|---|---|
| 4,501,273 | A | 2/1985 | McGinnis |
| 5,669,879 | A | 9/1997 | Duer |
| 2003/0236495 | A1* | 12/2003 | Kennedy, II .......... A61M 25/10 604/97.02 |
| 2004/0181206 | A1* | 9/2004 | Chiu .................... A61M 25/10 604/509 |
| 2006/0271087 | A1* | 11/2006 | Von Dyck ......... A61M 25/1018 606/192 |
| 2009/0145236 | A1 | 6/2009 | Esnouf |
| 2010/0179488 | A1 | 7/2010 | Spiegel |

FOREIGN PATENT DOCUMENTS

| | | |
|---|---|---|
| GB | 04241 | 9/2010 |
| WO | WO 2009/035366 | 3/2009 |

* cited by examiner

DEVICE FOR GRAVITY-DRIVEN CONTROL OF THE FILLING PRESSURE OF A CATHETER BALLOON

RELATED APPLICATIONS

This application is a 35 U.S.C. §371 national phase application of PCT/EP2013/056169 (WO 2013/139986), filed on Mar. 22, 2013, entitled "Device for Gravity-Driven Control of the Filling Pressure of a Catheter Balloon", which application claims the benefit of German Application No. 102012005643.5, filed Mar. 22, 2012, which is incorporated herein by reference in its entirety.

The invention relates to a device according to claim 1 as well as to a system according to claim 24.

Devices for a continuous, self-dependent (autonomous) control of the filling pressures in catheter balloons are in clinical use in various designs. Especially concerning catheter technologies that are associated with a long-term placement of a pressurized balloon component in the body, precise equipment that allows for an autonomous pressure control is required for the safe application of the product to the patient.

The long-term intracorporeal placement of a balloon catheter, for example, over days and weeks normally requires tissue effective filling pressures in the order of a few millibars (mbar). In case of a permanent exceedance of filling pressure values of about 30 mbar to 40 mbar or a permanent action of a corresponding force on perfusion sensitive structures an impairment of capillary perfusion or a tissue infarction resulting from the underperfusion may arise.

In order to generate and check the necessary balloon filling pressures required for the respective balloon function and in order to avoid unwanted exceedances or undershootings of the target filling pressure by corresponding readjustment, manually operated pump manometer are normally used for an easy management of the balloon filling pressure In principle, these manually operated systems do not allow for an independent, largely operator-independent management of the filling pressure. In order to prevent unnoticed filling pressure increases, manual pump manometers can be provided, depending on the design, with pressure relief valves, which forbid the rise of the filling pressure above a value predetermined by the valve. An independent active readjustment of the filling pressure in case of an occurred pressure can however not be guaranteed by such systems.

A control or management of the catheter balloon pressure that corresponds more appropriately to all requirements, particularly clinical requirements may be achieved with electronic pressure controllers. Electronic controllers usually perform an active pressure control. The steps "measuring" and "pumping" and/or "discharging" In repeat in short-term cycles. However, for the continuous measuring and control function a continuous supply of energy is necessary, for which a connection to the electricity network is usually required. The corresponding devices usually have a complex design, depend on maintenance, and are therefore expensive.

An alternative to manually operated pump manometers or electronic control systems are simple gravity-controlled systems in which by means of a weight applied to a compressible or deformable reservoir that is filled with a filling medium, a constantly acting filling pressure can be set in a catheter balloon communicating with this reservoir. A correspondingly controlled system is shown for example in WO9940960A1. In case of the device described therein, a pivoting beam-like supported arm device acts on a medium-filled reservoir balloon with a weight that can be adjusted in a variable manner. The beam resting on the reservoir bears a weight that can be displaced along the beam length, which, depending on the distance from the bearing point of the beam allows for setting a defined action of force on the reservoir. In case of an appropriately smooth-running and easily deformable volume reservoir, such a device allows for adjusting, in a relatively good approximation, a volume independent, constant filling pressure in a connected catheter balloon.

However, a disadvantage of this weight-controlled embodiment is the typically large necessary size of the device, especially when relatively large filling pressure ranges have to be covered. Further, depending on the respective adjusted angle or effective angle of the weight arm, a deviation of the action of force from the desired force value is to be expected. This angle depends on the respective filling state of the reservoir balloon or bellows. At a low volume level the angle is shallow, at a high volume level correspondingly steep. So, in case of a dynamically changing volume level in the reservoir balloon, for instance due to a transfer of laughing gas into the system, a particularly constant, volume independent action of force of the weight acting on the balloon cannot be reliably guaranteed in principle.

Further, the described device does in particular not comprise an indicator function, which indicates the respective pressure acting in the connected system communicating with the control device in a simple manner, and renders it comfortably readable for the user.

Thus, the problem underlying the present invention is to provide an improved device control of the filling pressure of a catheter balloon.

This problem is solved by a device according to claim 1.

According thereto, the device for gravity-driven (particularly continuous) control of the filling pressure in a balloon catheter, comprises: a balloon reservoir that is statically loaded with a vertically guided weight guide or stamp that weighs vertically on the balloon reservoir, wherein said weight guide or stamp is designed to carry vertically arranged and therewith plumb-vertically acting weight elements, and wherein the balloon reservoir is guided in a cylindrical shell.

Preferred embodiments of the invention are stated in the sub claims.

Particularly, the present invention describes a technically simplified, much more compact, weight-driven controller technology, particularly allowing for a constant pressure impingement of an integrated reservoir balloon over a wide volume range, and therewith essentially a particularly autonomously acting, technically robust and virtually maintenance-free, volume-independent management of a catheter balloon filling pressure.

Preferably, the control device according to the invention consists of simple basic elements that can be mounted in a few steps. Particularly, the correct assembly of the elements is simple, which largely prevents incorrect mounting. The elements are preferably virtually wear-free and have a long lifespan.

The essential principle of the controller described here consists in the static load of a balloon body (also denoted as balloon, balloon reservoir or reservoir balloon) by a vertically guided stamp (or stamp element or weight-guide) that weighs vertically on the balloon, which in turn carries vertically arranged or stacked and therewith plumb-vertically acting weights (or weight elements). Preferably, the balloon reservoir (or reservoir balloon) is housed in cup-like half-shells. Preferably, the half-shells guide the balloon in a cylindrical shell, which may consist of acrylic glass (e.g. Plexiglass). Particularly, the balloon reservoir is guided in the cup-like half-shells in a plumb-vertical manner.

Preferably, the guiding of the half-shells as well as of the guiding and weight elements resting on the upper half-shell takes place in the cylindrical shell.

Preferably, the reservoir balloon consists of a very thin-walled foil material, for example polyurethane (PUR). Polyurethane allows for forming of balloon foils of lowest wall thicknesses, which remain inherently stable even under load with higher filling pressures. Such balloons have, particularly in case of a corresponding thin-walled design, a membranous aspect, and show—upon filling and emptying of the balloon envelope—virtually no autonomous mechanics or action of force that is relevant or to be considered. The weight is therefore transmitted virtually loss-free to the filled reservoir balloon. The membrane-like thin-walled balloon body is preferably formed in a cylindrical shape which is adapted or largely adapted (particularly concerning the form and dimensions of the balloon) to the inner surfaces of the cup guide (e.g. the cup-like half-shells).

In the filled state of the balloon the latter deploys into the upper and lower cup inner surface, and presses the two half-shells butting perpendicularly against each other away from each other. The resulting gap between the shells is used as an indicator for a filling pressure acting in the system, which filling pressure is adjusted by the user by applying corresponding weights.

Particularly, in detail, upon successive filling starting from the unfilled state, the micro-thin-walled reservoir balloon unfolds in a space-filling manner into the cup halves (i.e. cup-like half-shells) butting against each other in a play-free manner as well as into their cavities. On reaching the complete filling of the respective cavity, and when exceeding the weight resting on the reservoir balloon from above, the two cup half-shells (i.e. cup-like half-shells) separate from one another in the plumb-vertical direction. The resulting gap between the reservoir balloon guiding shells serves as an indicator of the filling pressure acting in the system (reservoir balloon, catheter balloon and connecting hose system), and set by the user by applying appropriate weights (see above).

Preferably, in the filled state of the balloon, the upper and lower end of the reservoir balloon are inserted flush with the cavity of the upper and lower cup-like balloon guide (i.e. half-shell), whereby the reservoir balloon is precisely aligned longitudinally in the plumb line direction, and a contact of the balloon envelope with the cylinder inner wall (i.e. inner side of the cylindrical shell) can be avoided.

Preferably, in the emptied state of the reservoir balloon or in case of undershooting the system pressure preset by applying weights, the upper and lower cup half-shell butt against each other in a gap-free manner in the cylinder guiding the cups.

Preferably, due to the gap according to the invention between the balloon-guiding cup half-shells, an easy readability of the current effect or non-effect of the desired pressure or the pressure determined by application of weights in the communicating system of controller and catheter is guaranteed (even from a distance). In case the gap is present, the pressure acts; in case the two cup halves butt against each other play-free, the current system pressure is lower than the respective desired acting pressure.

The respective filling pressure is thereby, in case of an appropriate design of the balloon having a sufficient reserve volume or a sufficient cylindrical length, over a wide range independent of the amount of the filling volume introduced into the system.

Preferably, in case of forming of the reservoir balloon with a sufficient reserve volume or providing the balloon with a sufficient cylindrical length, the gap can be formed correspondingly high and can thus fulfill its function of indicating the pressure effectiveness over a wide volume range. Thus, also larger volume shifts can occur within the communicating system at a throughout constantly acting system pressure.

Particularly, the described principle of the volume-independent constant pressure works reliably as long as the envelope of the balloon body is not fully unfolded or is not completely and folding-free developed in the longitudinal direction or the envelope of the reservoir balloon does not reside in a stretched state. Preferably, the envelope shall be dimensioned such with respect to its length, that the cup guides release a gap of a height of preferably at least 1 cm up to 5 cm, wherein the balloon envelope remains in an unstretched state. For guaranteeing an unstretched balloon state and for securing the volume independent constant pressure according to the invention, the respective balloon filling volume which sets a gap height of 5 cm shall amount to merely ⅔ of the volume of the freely unfolded, non-stretched reservoir balloon volume.

In the non-filled state the balloon collapses on very thin wall layers. In case parts of the collapsed balloon envelope should get caught particularly between the face sides of the cup guides (i.e. cup-like half-shells), no gap will therefore be visible between the latter.

Particularly, the upwardly facing surface of the upper cup body (i.e. cup-like half-shell) ensures a defined force-effective support surface, which serves as a fixed reference point for the calculation of the pressure development in the balloon or system caused by the weight elements.

Alternatively, the adapted reception of the upper balloon end within the cavity of the upper cup member (i.e. cup-like half-shell), ensures a defined force—effective support surface, which serves as a fixed reference point for the calculation of the pressure development in the reservoir balloon and in the system communicating therewith, which is caused by the weight elements.

The present invention describes exemplary several possible versions of such a control device. In one embodiment the device is illustrated, mechanically complex, with precise, friction-reduced axial guide of stackable ring weights. In further embodiments alternative, simplified versions are described, wherein ball weights are used, which are in turn housed in a simple cup-like guide.

These controller versions are described as an example for the specific use of filling and control of the filling pressure of sealing cuffs of tracheal ventilation tubes, laryngeal masks and tracheal tubes for children.

Preferably, the weight guide weighing on the balloon body (upper half-shell, weight-receiving stamp; or weight-receiving rolling cross, also denoted as fall cross, with stamp; or weight-receiving ball cup) shall autonomously set, in a state in which it is not loaded with weights, a filling pressure of 5 mbar, alternatively 10 mbar, or preferably 15 mbar.

For tracheal blocking of tracheal tubes for children the required filling pressure, depending on the used tube model, particular lies in the range between 5 and 15 mbar, or is particularly 5 mbar.

By placing a weight element on the weight guide, wherein the weight of the element causes a pressure increase in the balloon body of 15 mbar, the tracheal blocking pressure can be raised, for example, to 20 mbar (which corresponds approximately to the upper desirable filling pressure in the case of the intubation of children), or can be raised from preferably 15 mbar to 30 mbar, which corresponds approximately to the required cuff sealing pressure in case of the tracheal intubation of adults.

Upon further intake of one or two identically sized weights, the resulting pressure force can to be increased to 45 mbar or 60 mbar. The filling pressure range between 45 mbar and 60 mbar corresponds to the filling pressures required for the blocking of laryngeal masks.

Alternatively to the division of the weights in 15 mbar acting units, also corresponding divisions in 10 mbar increments are possible, for example, wherein the weight-receiving units should in turn be preferably dimensioned such that they set a pressure of 10 mbar acting in the corresponding system when acting on the reservoir balloon in a state of rest of the latter, in which state of rest the balloon reservoir is not loaded with weights.

The division of the weight units is preferably carried out with uniformly sized weights, however, staggered sized weights having for example a weight effect of 10 mbar, 20 mbar and 30 mbar may also be used.

Preferably, the weight elements are preferably arranged on the upper side of the foot unit in corresponding recesses of the foot body.

Preferably, the respective embodiments of the invention autonomously balance volume fluctuations that arise in the course of a ventilation by means of a corresponding volume reservoir. The reading of the desired applied system filling pressure is simple and easily recognizable also from a distance.

Of particular importance for the functioning of the controller according to the invention is the technically simple presentation and readability of the system pressure prevailing in the reservoir balloon and catheter connected thereto due to gravity. In addition to the representation of the current system pressure as the gap between the balloon receiving cup halves, the respective prevailing system pressure determined by the application of weights can also be indicated by the passage of the upper end of the stamp through a closure element (or lid element) closing the cylinder (i.e. cylindrical shell) holding the components. In case the filling pressure prevailing in the system exceeds the respective weight applied, the free end of the stamp moves out through the through-opening of the closure element guiding the stamp and thus gets an indicator function.

In case the filling pressure undershoots the weight the upper end of the stamp is flush with the upper surface of the closure element. This indicating function can be used in combination with the indexing cup gap or may also be used independently and separately.

Particularly, the described control system is especially advantageous for catheter applications in which frequent physiological fluctuations of the organ diameter acting on the catheter balloon occur, as for example, in case of balloon placements within the esophagus or of parts of the small or large intestine. Likewise advantageously, the controller can be used in applications in which the catheter balloon is exposed to diffusible gases, which, without pressure-constant volume shift, lead to a security-relevant change in the balloon filling pressure acting on the organ, as can be observed in case of the laughing gas diffusion into the sealing cuffs of tracheal tubes. Further, the problem according to the invention is solved by a device having the features of claim 23 as well as a system having the features of claim 24.

According thereto, said system comprises a control device according to the invention, as well as a filling hose and a three-way valve, wherein the filling hose connects the three-way valve to the balloon reservoir.

Preferred embodiments of the system according to the invention are stated in the corresponding sub claims relating to the system.

In the following Figures exemplary embodiments and their respective functional groups are described.

Figure 1:
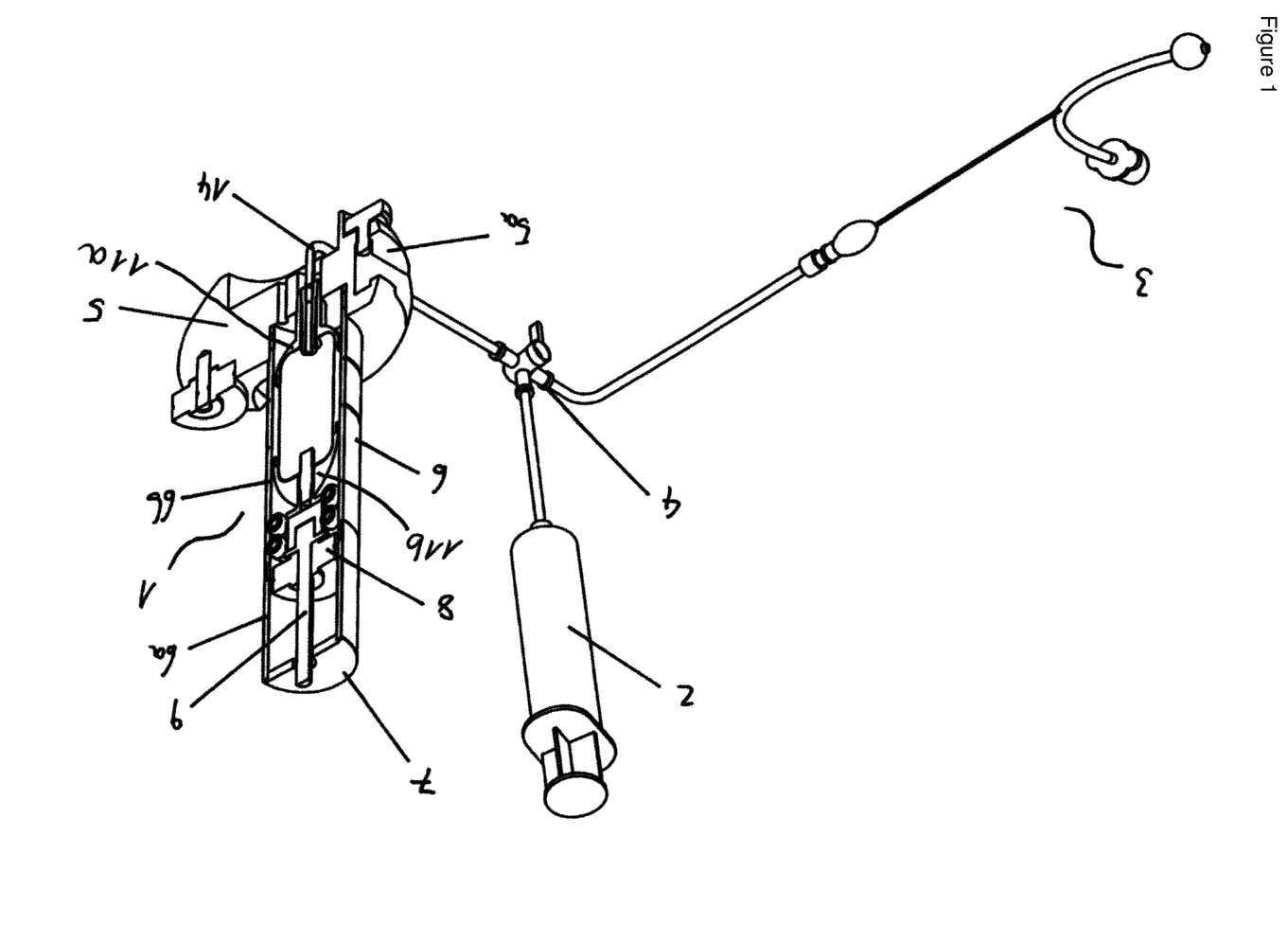
FIG. 1 shows an overview of the system, in which the controller unit is connected as an example with a low-pressure balloon catheter (ventilation tube) and a filling device (injection syringe)

FIG. 1 shows an overview of the system, wherein a device according to the invention (also denoted as controller or controller unit) 1 is connected via the filling device 2 (syringe element) with a balloon catheter 3 (tracheal tube). The filling by means of a separate filling device 2 is preferably carried out by means of a three-way valve 4. The valve 4 connects all system components, thus the controller 1, the catheter 3 connected to the controller 1 and the filling device 2 to a (particularly pressure-) communicating system. On the lateral leg of the valve 4 preferably a customary syringe 2 can be plugged on as a filling device 2, alternatively a pump balloon or a hand-operated pump manometer can be connected as well. The syringe volume is preferably chosen such that it facilitates a gap between the cup guides (i.e. cup-like half-shells 11a, 11b) of the balloon body (also denoted as balloon, reservoir balloon, or balloon reservoir) 10 of at least one centimeter, but as far as possible not more than 5 centimeters.

The foot unit or the foot plate 5 (e.g. having a diameter of 130 mm) of the controller 1 preferably consists of anodized aluminum and is configured such that it ensures the safe and vertical stand of the device 1. As a preferred embodiment the foot unit 5 is furthermore furnished with an integrated holding claw 5a for fastening to a usual clinic equipment rail.

The tube cylinder (i.e. cylindrical shell) 6 is vertically plugged into the foot unit 5 and (in the connection region) held free of clearance by means of an optional O-ring. On the bottom side the plate or foot unit 5 is preferably furnished with one or more millings and/or bores, which facilitate a (particularly strain-relieved) exiting of the filling hose 14 connected to the balloon reservoir 10 out of the device 1. The cylinder or cylinder tube 6 preferably consists of particularly transparent acrylic glass (e.g. Plexiglass) and is particularly chosen such with respect to its height and its inner diameter that all embodiments of the controller unit 1 can be implemented. Furthermore, in the embodiment shown here, the cylinder 6 comprises an upper cap segment 6a, which is plugged onto the lower cylinder segment 6b and closed upwards by means of a lid (i.e. closure element) 7. The length of the so segmented cylinder 6 is preferably chosen such that the surface of the lid element 7 in the non-impinged resting state of the system is flush with the upper free end of the stamp or stamp element 9 receiving the weights or weight elements 8.

Figure 2:
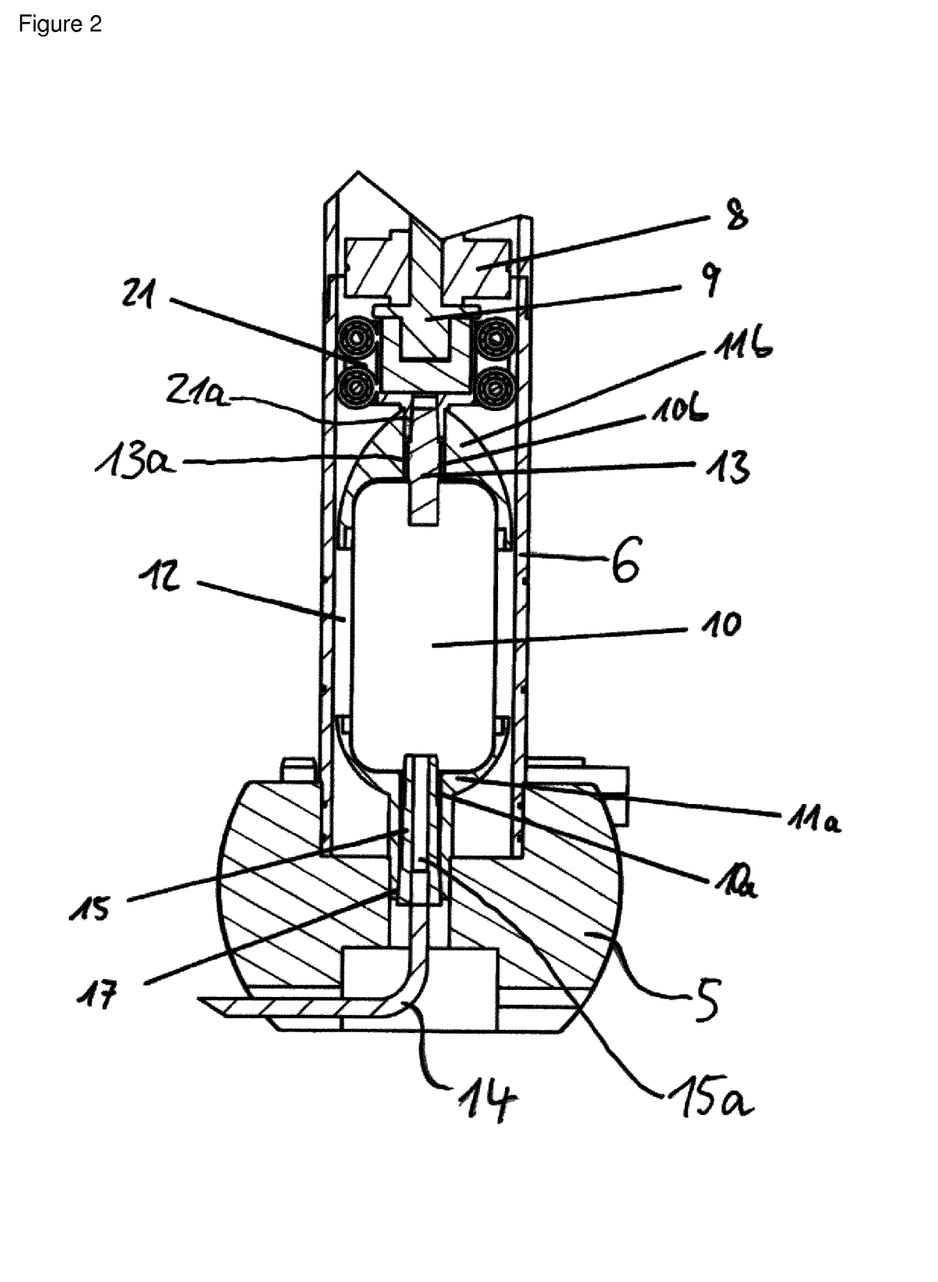
FIG. 2 shows the housing according to the invention of the reservoir balloon in a lower and upper cup guide and describes the configuration of the balloon with respect to the other controller components.

FIG. 2 shows in a preferred embodiment of the invention, how the particularly cylindrical shaped balloon body 10 is housed in the cup-like guides or half-shells 11a (lower cup) and 11b (upper cup).

The balloon body or balloon reservoir 10 preferably consists of a thin-walled, particularly little volume-stretchable polyurethane (PUR) having wall thicknesses ranging preferably from 5 micrometer to 20 micrometer. The balloon body 10 is preferably made from a material or PUR of Shore hardness 5OA to 95A and less preferred of Shore hardness 55D to 60D, which advantageously restricts its particularly radial volume stretchability in case of a filling using typically applied or prevailing pressures of up to ca. 100 mbar and secures the conservation and self-supporting keeping of its cylindrical shape even in the gap region 12 between the cup halves (i.e. cup-like half-shells) 11a, 11b. The balloon 10 is firmly sealingly bonded (i.e. glued) with its lower end 10a to a plug-like element 15 (also referred to as lower cone 15). The plug 15 comprises a continuous bore 15a for connection of a filling hose 14. The filling hose connection or the filling hose 14 of the filling pipe is particularly bonded into the lower end of the plug 15 (or end of the bore of the plug).

On its upper end 10b the balloon 10 is also firmly sealingly bonded to a plug-like element 13 (also referred to as upper cone 13). The binding plug 13 bonded into the upper end 10b particularly comes with a particularly conical shaped end, which is plugged into a corresponding bore 13a in the bottom of the upper cup 11b from the inside, and thus firmly connects-though manually detachable—the reservoir balloon 10 by means of a compression. Besides a compression of the plug 13 in the upper cup 11b the leading conical part of the plug 13 can reach through the cup 11b and can be plugged into a corresponding central bore 21a in the bottom of the fall cross or fall body 21 and thus support the connection between the fall cross 21 and the upper cup 11b.

The lower balloon end 10a also comprises a particularly conical shaped plug 15, which has a central bore 15a (see above), through which the balloon 10 is filled. The conical portion of the plug 15 is inserted from the outside into a corresponding conical bore 17 of the bottom surface of the lower cup 11a with slight compression and thus connects the reservoir balloon 10 with the lower cup 11a. The largest diameter of the upper plug 13 is selected such that it can be passed through the smallest diameter of the bore 17. By means of the cones it is thus possible to lead the reservoir balloon 10 through the bottom of the lower cup 11a into the upper cup 11b, to anchor the reservoir balloon there, and subsequently, by insertion of the lower cone into the bottom of the lower cup and in case of applied pressure force, to secure the reservoir balloon 10 in its position between the two cup elements 11a, 11b. The cones allow the easy replacement of the reservoir balloon 10. In a preferred manner, the entire air or pressure-leading system of the controller consists of an integrated unit out of sealingly and fixedly interconnected elements and will also be replaced as such.

To avoid a too rapid volume flow or exchange between the communicating reservoir balloon 10 and the catheter balloon 3, the fill hose 14 can also be equipped with a correspondingly small inner lumen, which acts throttling on the flow of the filling medium. A throttling effect can also be achieved by a correspondingly reduced diameter of bore 15a. Preferably, the throttling segment has an inner diameter ranging from 0.5 mm to 1.0 mm and has a length ranging from 5 mm to 10 mm.

Generally, to avoid an undesirably rapid volume flow or exchange between the compartments communicating with each other, the air leading hose portions of the controller can be provided at any point with a throttling element or a lumen reduction, which limits the volume flow.

Figures 2A, 2B:
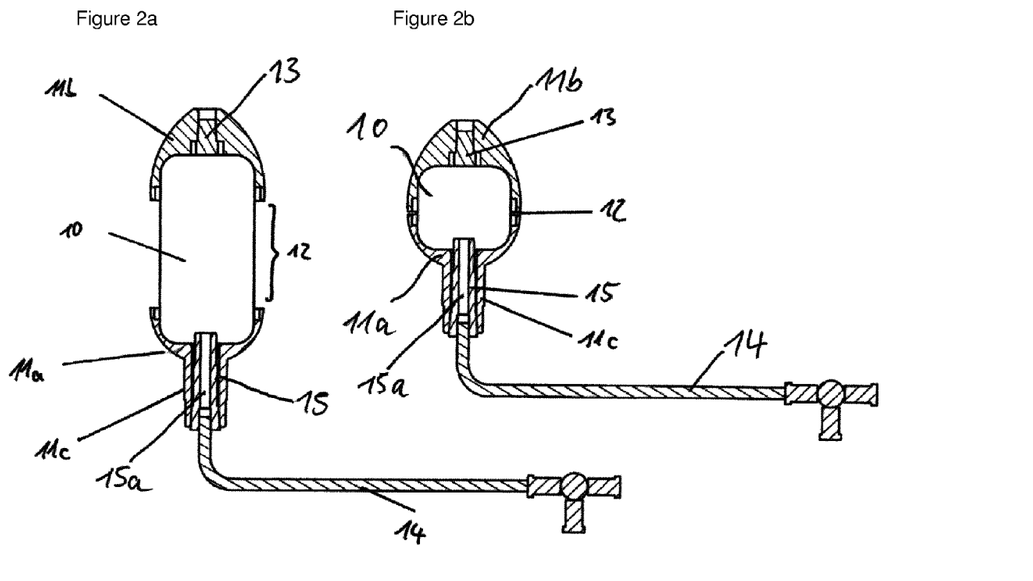
FIGS. 2a and 2b show the structural interaction of the reservoir balloon and the cup guides in the filled and emptied balloon state.

FIGS. 2a and 2b show exemplary the spatial accommodation of the reservoir balloon 10 in the balloon-guiding cup elements (i.e. cup-like half-shells) 11a and 11b in more detail, wherein the reservoir balloon 10 is shown in FIG. 2a completely filled and developed in its entire cylindrical length within the cup guides 11a, 11b. The cup gap 12 thus has its maximum extent. Upon further filling beyond the balloon volume corresponding to a free, stress-free deployment of the balloon 10, the balloon wall crosses over to a gradual expansion, and the balloon wall breaks out radially (i.e. in the radial direction) in the gap region.

FIG. 2b shows the balloon 10 in the state of rest, wherein the two cup halves 11a, 11b butt against each other substantially gap-free 12.

The upper and lower cones 13 and 15 are here directly pressed into the respective cup halves 11a, 11b.

For better visual readability of the respective outer cup contour (closed gap-free or opened with gap), the lower cup half 11a is preferably separated by a stamp-like extension 11c from the bottom of the foot unit 5, and is thus represented inside the cylinder nearly contour-closed, in a most free presentation.

The indicator function of the gap 12 occurring between the reservoir balloon-guiding cup halves 11a, 11b can be supported by a particular form of the balloon-holding cup. It has been found that the gap-based readability of the pressure action in the system is facilitated by a, for example, spherical or ovoid contour of the overall cup 11a, 11b. The respective sphere or egg shape breaking open upon forming of the gap 12 is intuitively recognized and registered as deviating from the normal state by the observing eye. The recognition of the shape deviation can be supported by an appropriately aggressive choice of color for the, for example, egg-shaped cup body.

Advantageously, the cup body 11a, 11b may be designed in a signal orange or yellow.

The indicator function of the gap 12 is advantageously supported by a clear transparent balloon body.

Figure 3:
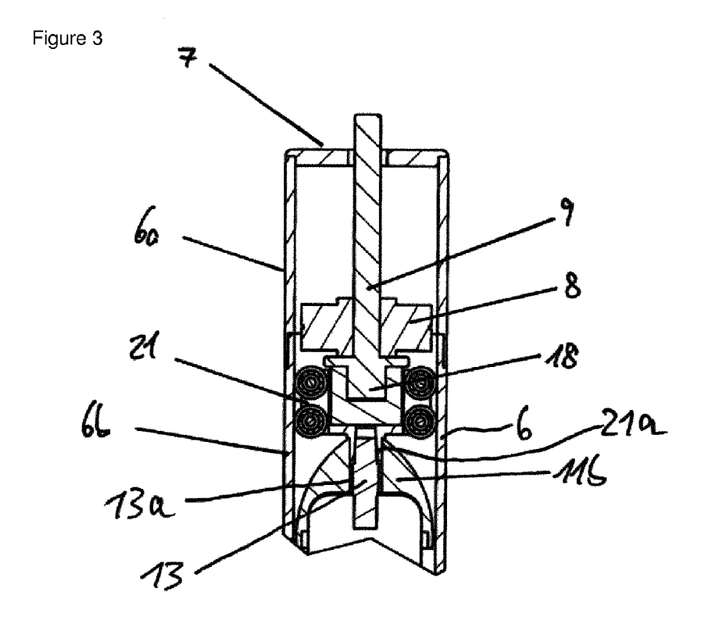
FIG. 3 describes in a special embodiment of the invention a vertical guide of the weights by means of a fall cross as well as a stacked reception of the weights by means of a stamp element, which can be placed on top of the fall cross.

FIG. 3 describes, in a notably particular embodiment of the invention, how the action of weight (e.g. the weight elements 8) can be transferred in a plumb-vertical manner to the (upper) cup guide 11b and, in particular, to the reservoir balloon 10 fixed in the latter. Here, the upper cup guide 11b optionally comprises a central bore 13a into which a plug-like connection member 13 is inserted, which makes the connection of the cup member 11b to a fall cross or fall body 21 facilitating the precise plumb-vertical guiding of the force-effective weights 8.

The roll guiding of the fall cross serves the precisely guided, vertical, largely frictionless guiding of the force-effective elements.

Figure 3A:
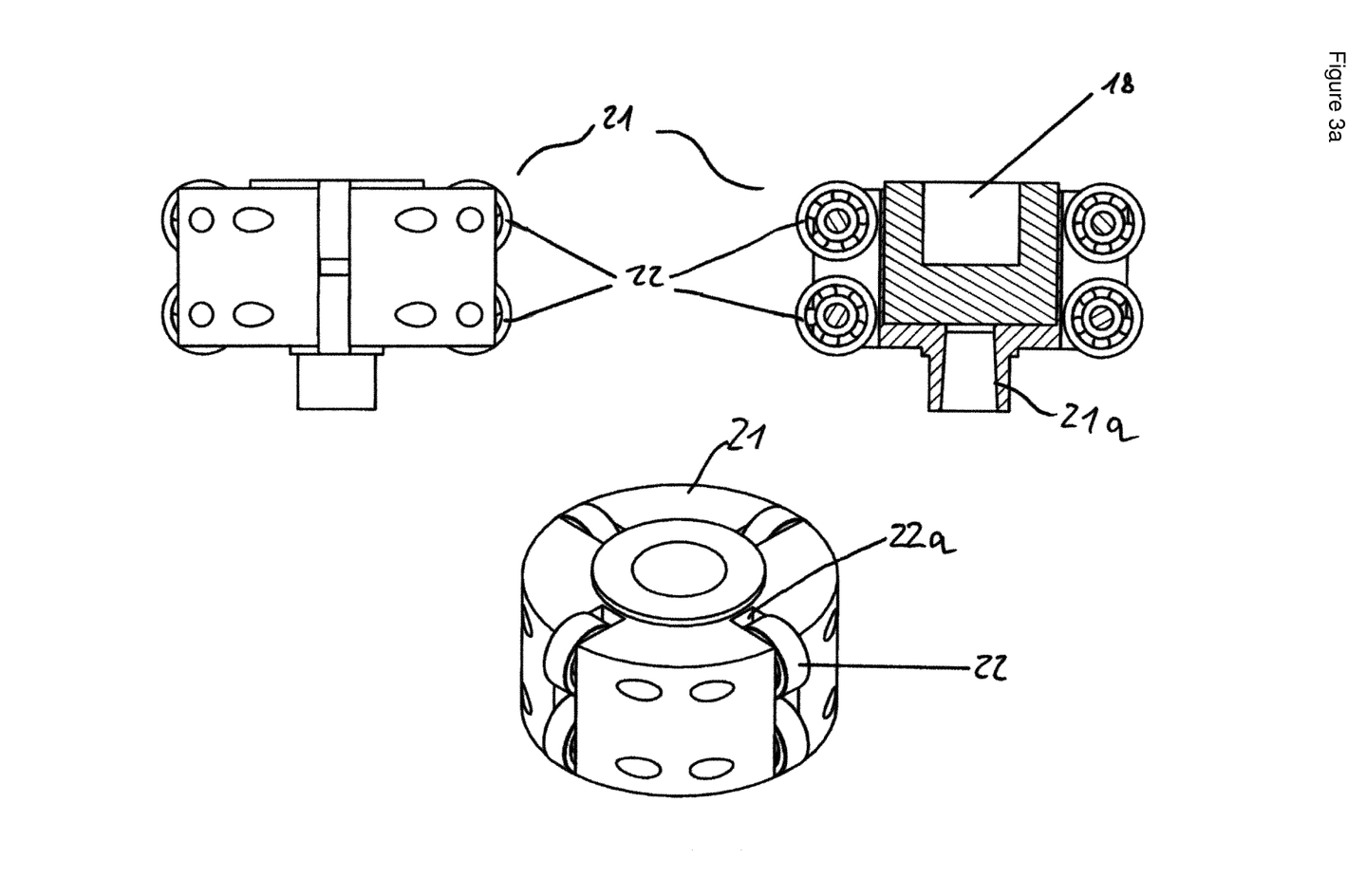
FIG. 3a shows a specific embodiment of a friction-reduced gliding wheel-supported fall cross.

The fall cross 21 preferably has an outer roll guiding facing towards the cylinder inside by means of several low-friction supported ball or wheel elements 22 (see FIG. 3a). Preferably, the cross 21 comprises four legs or recesses 22a that are particularly arranged at right angles with respect to each other as shown in FIG. 3a, wherein each leg or recess 22a comprises two roll-like elements 22, which guide the cross 21 on the inner wall (e.g. on the inside) of the cylinder 6. The fall cross 21 comprises an optional central bore hole 18, which receives a handle element 9 (also denoted as stamp or stamp element) upwardly, which serves for receiving the weight rings 8. The handle member 9 is connected to the fall cross without play, but can be well released from each other. It can be removed at any time from the cylinder upwards, and can be provided with the respectively required weights.

Generally, the fall cross or body 21 may have a cylindrical shape as shown in FIG. 3a with four recesses 22a receiving the ball or wheel elements 22, wherein the regions comprising the recesses 22a may also form protrusions (e.g. legs at right angles) such that the fall cross 21 actually comprises a cross-like cross section.

Alternatively, the fall cross 21 comprises an optional central through-bore hole, which, on the lower side, connects to the upper cup member 11b, and receives said handle element 9 (also denoted as stamp or stamp element) upwardly, which serves for receiving the weight rings 8.

The upper cup guide 11b is thus connected to the stamp (also denoted as stamp element or handle element) 9 receiving the weights via a special element, here a so-called fall cross 21, which allows for the plumb-vertical guiding of the elements acting force-effectively on the balloon 10.

In the non-loaded, gap-free state of the device 1, the tip of the stamp-like handle element 9 is flush with the surface of the lid element (or closure element) 7 closing the cylinder upwards. In case the cup halves 11a, 11b separate from each other and a gap develops between them, a corresponding exit of the tip of the shaft of the stamp 9 through the through-opening in the lid element 7 occurs, which represents a further optional function indicating the pressure effect set in the system.

Figure 4A:
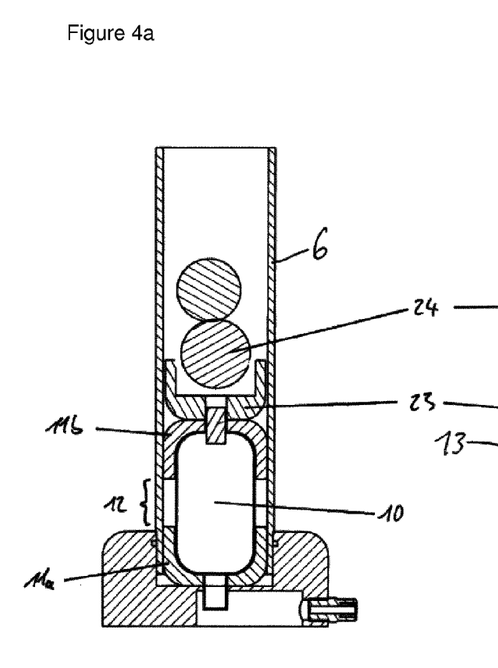
FIGS. 4a and 4b show as an alternative to the embodiment comprising a fall cross a simple cup guide for receiving ball weights.

FIG. 4a shows as (structurally less complex) alternative to the fall cross or body 21 a simple cup-like device 23 or cup guide 23 for receiving one or a plurality of ball weights 24. The cup guide or cup-like device is optionally connected by a connecting element, for example a pin, on the lower surface to the upper balloon guiding cup. For a better or friction-reduced guiding of the ball-receiving cup 23, the latter can be alternatively applied on a fall cross as described in FIG. 3.

Figure 4B:
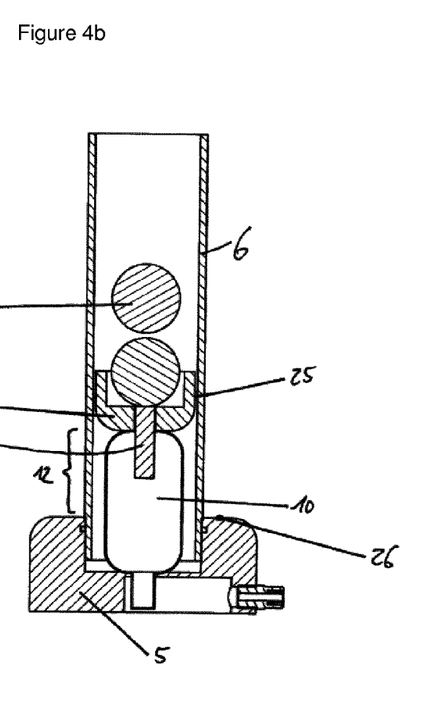

However, in a less preferred embodiment, as shown in FIG. 4b, one may completely dispense with a cup-like guide 11a, 11b of the reservoir balloon 10. Here, the balloon 10 can be fastened through the plug 13 directly in the bottom of the ball-receiving cup 23. In order to avoid that in case of a missing cup guiding of the balloon wall portions of the balloon 10 get caught in the slit 25 between the cylinder inner wall and the ball cup outer wall thus blocking the free run of the cup 23 inside the cylinder 6, the slit 25 should be designed correspondingly wide and should amount to 1 mm for example. In the absence of a guiding of the balloon 10 by means of appropriate cup elements 11a, 11n, the readability of the pressure-indicating gap 12 can be ensured as well in this simplest embodiment, by designing the bottom of the cup 25 such that it is flush with the surface 26 of the foot unit 5 in a non-impinged state. In case the filling pressure in the balloon 10 overcomes the applied weight pressure, a readable gap 12 develops in case of increasing filling volume.

Figure 5:
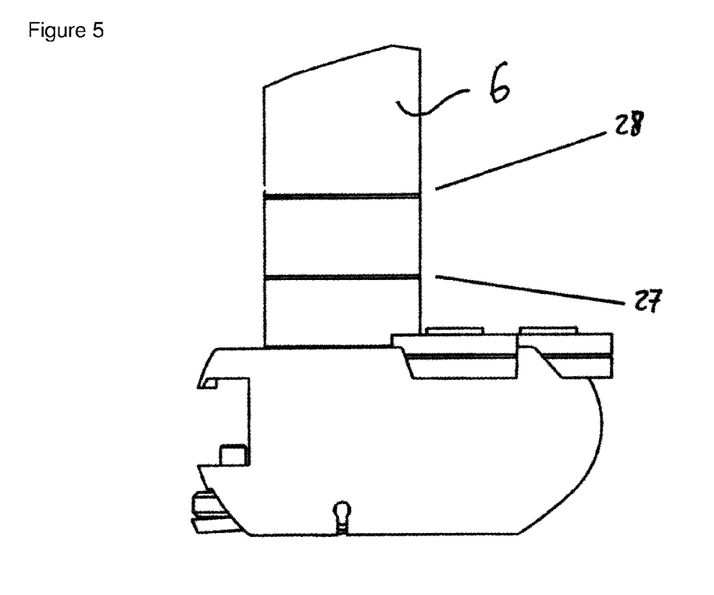
FIG. 5 describes preferred volume markings on the cylinder body (i.e. cylindrical shell)

FIG. 5 shows annular markings 27 and 28 of the cylinder 6, which on one hand (27) represent an optimal volume reserve in the communicating system, which is to be set, and on the other hand (28) marks a volume, which should not be exceeded, in order to avoid an upward development of the balloon 10 in the range of a complete longitudinal extent as far as possible. The ring 27 should be placed approximately 1 cm to 2 cm above the upper edge of the lower cup 11a, the ring 28, however, should be preferably spaced apart from the other ring 27 by about 3 cm to 4 cm. The remaining distance up to the complete deployment height of the balloon 10 should amount to, starting from the ring marking 28, about 2 cm to 3 cm.

Figure 6:
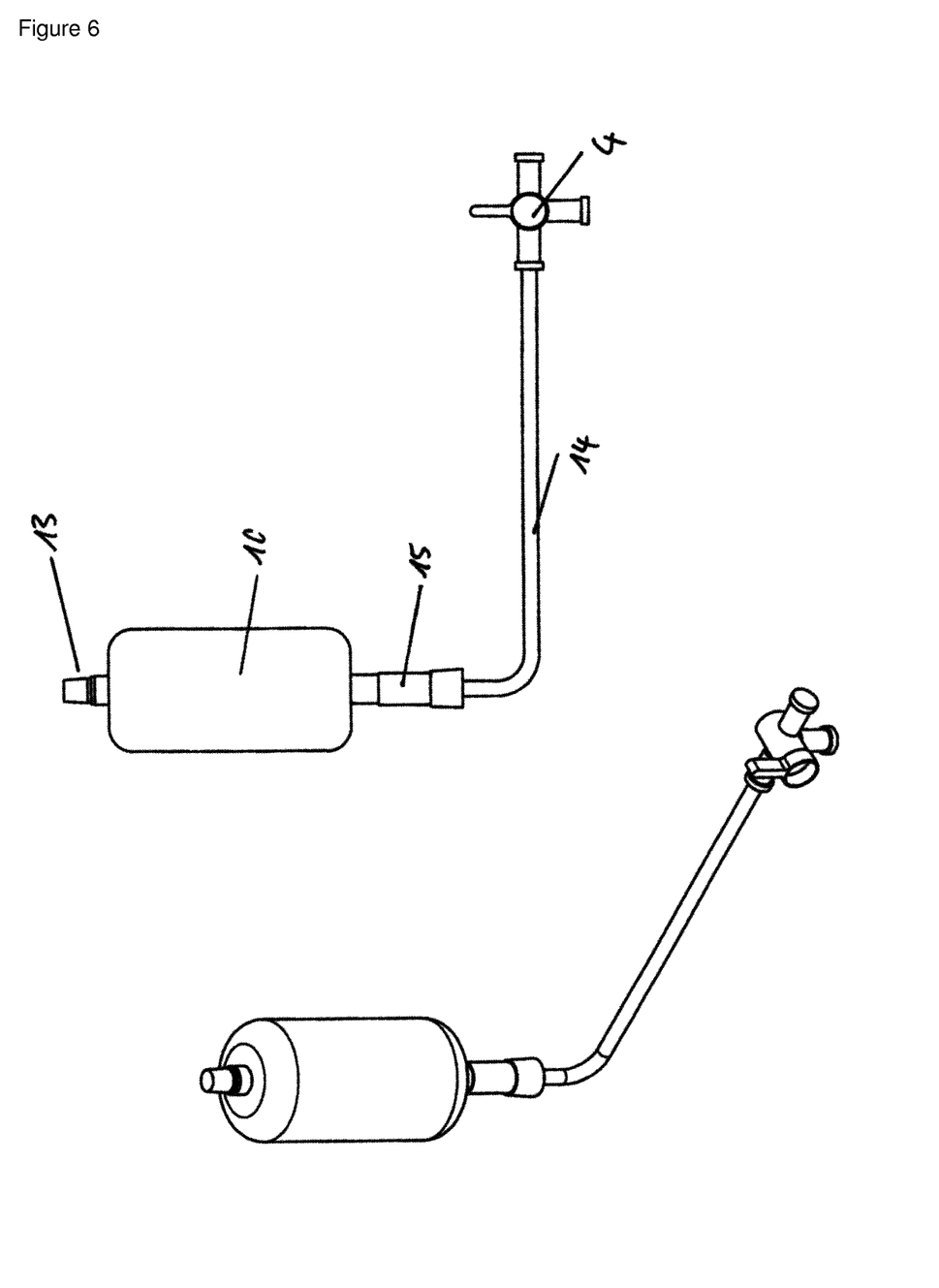
FIG. 6 shows an embodiment of the pressure or volume receiving system built as a continuous unit.

In FIG. 6, the entire air-guiding system of the controller 1 is shown as an exemplary unit. The balloon 10 is connected to the two cones 13 and 15 in a sealing manner, the filling line 14 is sealingly inserted into the cone 15, and is in turn connected permanently and sealingly to the valve 4. The entire illustrated unit thus allows, if necessary, the rapid change of the air-conducting system.

Figure 7:
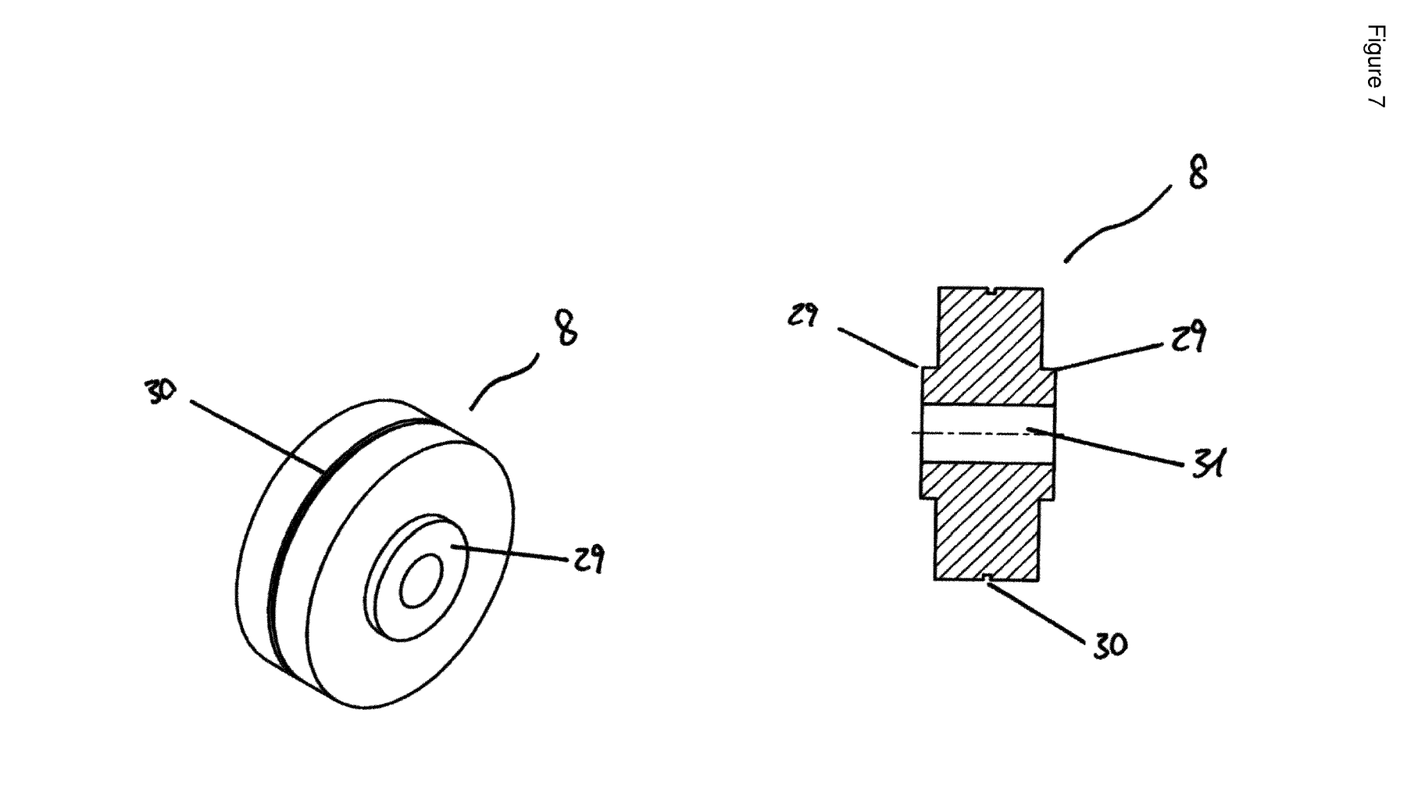
FIG. 7 shows exemplary ring weights.

FIG. 7 shows a particular embodiment of annular weights 8, as they may be used in combination with a stamp-shaped receiving element 9. The ring 8 has a central bore hole 31 for receiving the shaft of the stamp. Preferably, the ring comprises reduced diameters 29 (recesses) on the upper and lower side deviating from the central, largest diameter. During stacking on the stamp, this results in a slit between the respective weight rings separating the units that facilitate the countability of the units for the user. The ring may also comprise circumferential millings 30 that are filled with color, so as to allow for an easy to read color coding of the respective weight of the units.

Preferably, all elements resting on the reservoir balloon in the described embodiments, with the exception of the variable weight elements, are preferably made of aluminum or PEEK, and are preferably calculated such concerning their mass that preferably a pressure-effective weight results, which when resting on the balloon body, generates a pressure of particularly 15 mbar in the latter. The weights (weight rings and balls) are preferably made of high quality or stainless steel. Each individual weight element 8, 24 is in turn preferably dimensioned such that when it is applied, a respective pressure increase of 15 mbar is established.

Example 1

In the following, for the described embodiment of the fall cross base, some examples of weight and pressure calculations are shown.

The aim is setting a pressure in the reservoir balloon 10 of 15 mbar in the state, in which the balloon 10 is not loaded with weights 8. Assuming a force-receiving cross-sectional area of the balloon of 907.9 mm$^2$ (0.000908 m$^2$), which corresponds to a cylindrical balloon diameter of 34 mm, a weight of approximately 1.41 N is required for this, which corresponds to a mass of 144 g (0.144 kg).

Depending on the respective material used for the stamp 9, the fall cross 21 and the upper cup guide 11b, the mass of the components must yield 144 g in total.

The ring weights 8 applied to the stamp 9 consist for example of high quality or stainless steel of grade 1.4301, with a density of 7.9 kg/m$^3$. For causing a system pressure rise of 15 mbar in the system, a discoid weight element as shown in FIG. 7 with a diameter of 40 mm has a height of about 17 mm (taking into account a central bore hole in the stamp of 8 mm).

FURTHER EXAMPLES

In another example the ring weights consist of high quality or stainless steel of grade 1.4301, with a density of 7.9 kg/m³

All other parts acting on the balloon are made out of PEEK and have a density of 1.32 g/cm³.

Calculation of the force action in the non-loaded state of rest (without applied weights):

| Name | Density g/cm³ | Volume cm³ | Masse g |
|---|---|---|---|
| Upper balloon guide (11b) | 1.32 | 13.222 | 17.45 |
| Upper plug (13) | 1.32 | 3.796 | 5.01 |
| Fall cross (21) | 1.32 | 16.838 | 22.22 |
| Roll (22) | 1.32 | 0.531 | 5.61 |
| Pin (connection roll/cross) | 1.32 | 0.1414 | 1.49 |
| handle (9) | 1.32 | 9.332 | 12.32 |
| Sum | | 43.8615 | 64.10 |

The weight required to generate a pressure of 5 mbar is calculated as follows:

$$F_g(5 \text{ mbar}) = P \times A$$
$$= 500 \frac{N}{m^2} \times 0.00125664 \text{ m}^2$$
$$= 0.628 \, N$$
$$= 0.628 \frac{kgm}{s^2}$$

Mass in kg:

$$m = \frac{F_g}{g} = \frac{0.628 \, N}{9.81 \frac{m}{s^2}} = 0.0640489 \text{ kg} = 64.04 \text{ g}$$

The upper cup-like balloon guide (11b) of Ø40 mm rests on the balloon with a force-effective circular area of 1256.64 mm². The calculation is as follows:

Balloon Guide Pressure Area:

$$A = \pi \times 20^2 \text{ mm}^2 = 1256.64 \text{ mm}^2$$

Pressure g/cm²:

$$p = \frac{m}{A} = \frac{64.03 \text{ g}}{12.5664 \text{ cm}^2} = 5.09 \frac{g}{cm^2}$$

The pressure sum generated by the PEEK-elements (without load provided by the weights) thus amounts to 5 mbar: 5.002 mbar.

Calculation of the force action of the ring weights out of V2A

| Name | Density g/cm³ | Volume cm³ | Mass g |
|---|---|---|---|
| Weight ring | 7.9 | 16.16 | 127.69 |

For a weight element out of high quality or stainless steel generating 10 mbar the following required mass is calculated:

$$m = \left(\frac{D^2 \times \pi}{4} - \frac{d^2 \times \pi}{4}\right) \times h \times \rho$$

$$m = \left(\frac{3.85^2 \text{cm}^2 \times \pi}{4} - \frac{1.05^2 \text{cm}^2 \times \pi}{4}\right) \times 1.5 \text{ cm} \times 7.9 \frac{g}{cm^2}$$

$$= 127.69 \text{ g}$$

Pressure g/cm²: $p = \frac{m}{A} = \frac{127.69 \text{ g}}{12.5664 \text{ cm}^2} = 10.16 \frac{g}{cm^2}$ Another example for the cup variant having ball weights By means of respectively one ball weight (22) the filling pressure in the system can be increased, respectively, by 10 mbar.

Force Action in the non-loaded state of rest (without weights)

| Name | Density g/cm³ | Volume cm³ | Mass g |
|---|---|---|---|
| Cup guide (23) | 1.32 | 35.29 | 46.58 |
| Upper balloon guides | 1.32 | 13.22 | 17.40 |
| Sum | | 48.51 | 64.03 |

Pressure g/cm²:

$$p = \frac{m}{A} = \frac{64.03 \text{ g}}{12.5664 \text{ cm}^2} = 5.09 \frac{g}{cm^2}$$

The ball weights are made out of high quality or stainless steel and shall generate a balloon or system pressure of 10 mbar by means of their weight.

| Name | Density g/cm³ | Volume cm³ | Mass g |
|---|---|---|---|
| Ball weight (24) | 7.9 | 16.21 | 128.06 |

Ball volume:

$$V = \frac{D^3 \times \pi}{6} \text{ in mm}^3$$

Diameter of a ball out of V2A for 10 mbar:

$$D = \sqrt[3]{\frac{m \times 6}{\rho \times \pi}} = \sqrt[3]{\frac{0.12806 \text{ g} \times 6}{7.9 \frac{kg}{dm^3} \times \pi}} = 0.34 \text{ dm} = 31.4 \text{ mm}$$

Diameter is 31.4 mm

As an alternative to the standard embodiment of the device having a foot, the controller can also be equipped with a C-shaped holding mechanism for mounting it to usual device holders in the operating room (mounting rail).

The invention claimed is:
1. A device for gravity-driven control of a filling pressure in a balloon catheter, comprising: a balloon reservoir that is statically loaded with a vertically guided weight guide that weighs vertically on the balloon reservoir, wherein said weight guide is configured to carry vertically arranged and therewith plumb-vertically acting weight elements, wherein the balloon reservoir is guided in a cylindrical shell, wherein the balloon reservoir is housed in two cup-like half-shells, and wherein said half-shells guide the balloon reservoir in the cylindrical shell.

2. The device as claimed in claim 1, wherein the balloon reservoir is housed in a lower cup-like half shell and an upper cup-like half shell.

3. The device as claimed in claim 2, wherein the two cup-like half-shells each comprise an inner surface, wherein the balloon reservoir is designed to deploy in a filled state of the balloon reservoir into the inner surfaces, and to push the two half-shells apart, so as to generate a gap between the half-shells, said gap serves as an indicator for the filling pressure in the balloon reservoir adjusted by a user.

4. The device as claimed in claim 2, wherein in a deflated state of the balloon reservoir or when a preset filling pressure is undercut, the two cuplike half-shells butt against each other, via a collapsed envelope of the balloon reservoir, in the cylindrical shell guiding the cup-like half-shells.

5. The device according to claim 2, wherein the balloon reservoir is formed in an elongated or cylindrical shape and is adapted to inner surfaces of the cup-like half shells.

6. The device according to claim 2, wherein the balloon reservoir comprises a cylindrical length that allows for generating a gap between the cup-like half-shells in the range from 1 cm to 5 cm in a filled but unstretched state of an envelope of the balloon reservoir.

7. The device as claimed in claim 2, further comprising the upper cup-like half-shell is connected to a fall cross being designed to plumb-vertically guide said weight elements, wherein the upper cup-like half-shell comprises a central bore hole into which a plug-like connection member is inserted, which connects the upper cup-like half-shell to said fall cross.

8. The device as claimed in claim 7, wherein the fall cross comprises four legs or recesses, each leg or recess comprising at least one roll-like element, which guides the fall cross on an inner side of the cylindrical shell, wherein the fall cross is connected to said weight guide, wherein the fall cross comprises a through-borehole; a lower side of the fall cross connects to the upper cup-like half-shell and an upper side of the fall cross receives said weight guide; said weight guide is configured to receive said weight elements in the form of weight rings, and wherein said weight guide is connected to the fall cross, substantially without play, so that said weight guide can be released from the fall cross and removed upwards from the cylindrical shell for providing said weight guide with the respectively required weight elements.

9. The device according to claim 2, wherein an outer visible surface of the cup-like half-shells comprises a signal colour.

10. The device according to claim 2, wherein the cylindrical shell comprises a closure element for closing an upper opening delimited by an upper face side of the cylindrical shell, wherein the closure element comprises a central through-opening for receiving a free end of the weight guide, wherein the free end of the weight guide protrudes out of the cylindrical shell through said through-opening when a gap is present between the two cup-like half-shells.

11. The device according to claim 2, wherein the cylindrical shell comprises at least one of a first marking indicating a minimum gap height of a gap between the two cup-like half-shells, particularly allowing for easy visual recognition of the gap and corresponding to a sufficient volume reserve, or a second marking indicating a maximal gap height of a gap between the two cup-like half-shells, selected such that the balloon reservoir is not fully deployed along its longitudinal axis when the maximal gap height is reached, so as to avoid stretching of an envelope of the balloon reservoir.

12. The device according to claim 1, further comprising the balloon reservoir is at its lower end bonded in a firm and sealing manner with a plug-like member, which comprises a continuous bore hole for connecting to a filling hose, wherein said hose connection is bonded into a lower end of the plug-like member.

13. The device as claimed in claim 1, wherein the weight guide comprises a vertically guided stamp that weighs vertically on the balloon reservoir, wherein said stamp is designed to carry vertically arranged and therewith vertically acting weight elements.

14. The device as claimed in claim 1, wherein the weight guide comprises a guide cup for receiving weight elements.

15. The device as claimed in claim 14, wherein the guide cup is connected to an upper cup-like half-shell, wherein the guide cup is connected on a lower side by a pin to the upper cup-like half-shell.

16. The device as claimed in claim 14, wherein the guide cup is connected to an upper end of the balloon reservoir, wherein the upper end of the balloon reservoir is connected to a bottom of the guide cup by means of a plug-like member, and wherein the balloon reservoir is vertically guided in the cylindrical shell by the guide cup.

17. The device according to claim 1, wherein the balloon reservoir comprises an envelope having a thickness in the range of 5 μm to 20 μm.

18. The device according to claim 1, wherein the cylindrical shell is made out of a transparent material.

19. The device according to claim 1, characterized in that the balloon reservoir consists of a thin-walled foil material having a Shore hardness in the range of 55D to 60D so as to restrict the radial stretchability of the balloon reservoir for filling pressures up to 100 mbar, such that the balloon reservoir does not contact an inner side of the cylindrical shell when being in a filled state with a filling pressure of up to 100 mbar.

20. The device according to claim 1, wherein the balloon reservoir is made out of a transparent material.

21. The device according to claim 1, characterized in that the weight elements are designed to be vertically arranged on top of each other on the weight guide so that a visible gap exists between adjacent weight elements, allowing for easy counting of the weight elements, wherein the weight elements comprise a weight used in clinical practice.

22. A system comprising:
a device for gravity-driven control of the filling pressure in a balloon catheter, wherein the device comprises a balloon reservoir that is statically loaded with a vertically guided weight guide that weighs vertically on the balloon reservoir, wherein said weight guide is configured to carry vertically arranged and therewith plumb-vertically acting weight elements, wherein the balloon reservoir is guided in a cylindrical shell, wherein the balloon reservoir is housed in two cup-like half-shells, and wherein said half-shells guide the balloon reservoir in the cylindrical shell;
a filling hose; and
a three-way valve, wherein the filling hose connects the three-way valve to the balloon reservoir.

23. The system according to claim 22, further comprising a filling device, in the form of a syringe, for filling the balloon reservoir with a medium, and a balloon catheter, wherein said three-way valve is designed to connect the balloon catheter, the filling device and the control device, so as to form a communicating system, and wherein a syringe volume for receiving said medium is selected such that is allows for adjusting a gap between the cup-like half-shells in the range of 1 cm to 5 cm when injecting the medium into the balloon reservoir by means of the syringe via the three-way valve.

24. The system according to claim 22, characterized in that the balloon reservoir is permanently connected to the filling hose in a sealing manner, and in that the filling hose is permanently connected to the three-way valve in a sealing manner, so that the balloon reservoir, the filling hose and the three-way valve form a permanently connected unit that is designed to be replaced as a whole.

* * * * *